United States Patent

Oka et al.

[11] 4,066,648
[45] Jan. 3, 1978

[54] ISOCHROMAN DERIVATIVES

[75] Inventors: Yoshikazu Oka, Kobe; Akio Miyake, Takatsuki; Norio Tada, Akashi; Katsumi Itoh, Takatsuki, all of Japan

[73] Assignee: Takeda Chemical Industries, Ltd., Japan

[21] Appl. No.: 690,928

[22] Filed: May 28, 1976

[30] Foreign Application Priority Data

Jan. 1, 1976 Japan .................................. 51-1243

[51] Int. Cl.² .......................................... C07D 405/06
[52] U.S. Cl. ...................... 260/268 TR; 260/268 BC; 260/293.55; 260/345.2; 424/250; 544/151
[58] Field of Search ........ 260/268 BC, 345.2, 268 TR

[56] References Cited

U.S. PATENT DOCUMENTS

| 3,467,675 | 9/1969 | Petersen et al. | 260/345.2 |
| 3,743,659 | 7/1973 | Klohs et al. | 260/345.2 |
| 3,840,562 | 10/1974 | Bolger et al. | 260/345.2 |

Primary Examiner—Paul M. Coughlan, Jr.
Attorney, Agent, or Firm—Wenderoth, Lind & Ponack

[57] ABSTRACT

New isochroman derivatives which may be represented by general formula [I]

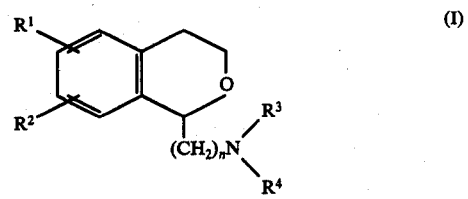

wherein $R^1$ is hydrogen atom, a lower alkoxy group or hydroxyl group and $R^2$ is a lower alkoxy group or hydroxyl group; $R^1$ and $R^2$ may also be, connecting with each other, alkylenedioxy group; $R^3$ is a hydrogen atom, a lower alkyl or aralkyl group and $R^4$ is a lower alkyl or aralkyl group; $R^3$ and $R^4$ may also be groups which, taken together with the adjacent nitrogen atom, form a cyclic amino group; $n$ means 1 or 2, and pharmacologically acceptable salt thereof have antidepressant, analgesic, diuretic, anti-inflammatory, muscle relaxing, vasodilator, hypotensive and other pharmacologic activities for mammals.

24 Claims, No Drawings

ISOCHROMAN DERIVATIVES

There have been few reports on isochromans carrying substituents on their benzene rings. All that is known to us pertains to the synthesis of isochroman having one or two methoxy groups on its benzene ring as reported in Journal of the Organic Chemistry 27, 4337 (1962) and Tetrahedron 27, 2615 (1971) but the synthesis was made solely from chemical curiosity, no investigation having been undertaken on the pharmacological activity of such compounds.

We synthesized a number of novel isochroman compounds having various substituents on their benzene ring moieties and made intensive studies on their pharmacological actions. The studies les us to the finding that compounds which may be represented by general formula (I):

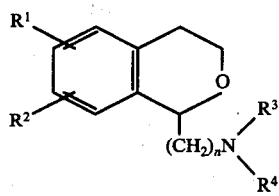
(I)

wherein $R^1$ is hydrogen atom, a lower alkoxy group or hydroxyl group and $R^2$ is a lower alkoxy group or hydroxyl group; $R^1$ and $R^2$ may also be, connecting with each other, alkylenedioxy group; $R^3$ is a hydrogen atom, a lower alkyl or aralkyl group and $R^4$ is a lower alkyl or aralkyl group; $R^3$ and $R^4$ may also be groups which, taken together with the adjacent nitrogen atom, form a cyclic amino group; $n$ means 1 or 2, and pharmacologically acceptable salt thereof have pharmacological actions and, therefore, are of value as medicines.

Referring to the above general formula, the lower alkoxy groups $R^1$ and $R^2$ are exemplified by ones containing 1 to 4 carbon atoms such as methoxy, ethoxy, n-propyloxy, i-propyloxy, n-butyloxy, i-butyloxy, sec-butyloxy, tert-butyloxy and so forth. As alkylenedioxy group which is formed by connection of $R^1$ and $R^2$, there may be mentioned a lower alkylenedioxy groups containing not more than three carbon atoms such as methylene dioxy, ethylenedioxy and propylenedioxy.

As examples of alkyl groups $R^3$ and $R^4$, there may be mentioned alkyl groups containing not more than six carbon atoms such as methyl, ethyl, n-propyl, i-propyl, n-butyl, i-butyl, sec-butyl, tert-butyl, n-pentyl, n-hexyl and so forth. The aralkyl groups $R^3$ and $R^4$ may be aralkyl groups of 7 to 10 carbon atoms such as benzyl, phenethyl, α-methylbenzyl, α-methylphenethyl and so forth. Where $R^3$ and $R^4$ form a cyclic amino group with the adjacent nitrogen atom, the cyclic amino group is exemplified by cyclic amino groups containing a 4 to 6-membered ring, such as azetidinyl, pyrrolidinyl, piperidino, porpholino, piperazinyl and so forth. Such a cyclic amino group may also have one or more substituents on its ring. Thus, the substituents may occur in optional positions on the ring and, may for example be lower alkyl groups of 1 to 4 carbon atoms, e.g. methyl, ethyl, n-propyl, i-propyl, n-butyl, tert-butyl, etc., aryl groups such as phenyl, naphthyl, etc. aralkyl groups such as benzyl, benzhydryl, phenethyl, α-methylbenzyl, etc., 5- or 6-membered heterocyclic groups including one or more nitrogen, oxygen and/or sulfur atoms as heteroatoms, e.g. pyridyl, thienyl, furyl, etc. and aliphatic, aromatic and heterocyclic acyl groups such as acetyl, propionyl, benzoyl, naphthoyl, nicotinoyl, furoyl and so forth. These and other substituents may further have 1 to 3 substituents such as halogens, e.g. chlorine, fluorine, iodine, etc., lower alkoxy groups of 1 to 5 carbon atoms, e.g. methoxy, ethoxy, propoxy, ethylenedioxy, etc., and so forth.

The compound according to the present invention may for example be produced by reacting a compound of the general formula:

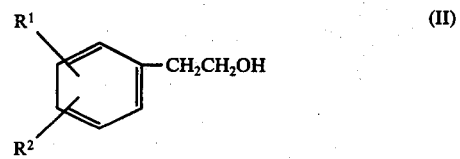
(II)

wherein $R^1$ and $R^2$ have the same meaning as above with a compound of the general formula:

$$OHC-(CH_2)_n-Y$$ [III]

wherein Y is a halogen atom such as chlorine, bromine and fluorine; $n$ has the same meaning as above to obtain a compound of the general formula:

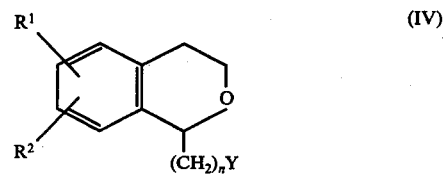
(IV)

wherein $R^1$, $R^2$, Y and $n$ have the same meanings as defined above and, then, reacting the last-mentioned compound with an amine of the general formula:

(V)

wherein $R^3$ and $R^4$ have the same meanings as defined above.

The compound of general formula [III] employed in the aforementioned reaction of compound [II] with compound [III] may as well be a derivative thereof in a form such that its aldehyde group has been protected, such as an acetal or hemi-acetal compound.

This reaction is conducted either in the presence of a solvent or in the absence thereof. Where a solvent is employed, it may be any of the solvents that will not interfere with the contemplated reaction, e.g. water, ethanol, methanol, chloroform, benzene, dimethylformamide, tetrahydrofuran, etc. and mixtures of two or more of such solvents. Where either compound [II] or compound [III] is liquid at the reaction temperature, the liquid compound may be used in excess so that it may act also as a solvent. An appropriate reaction temperature may be selected from within the range of $-10°$ to $+250°$ C, although the range of $+20°$ to $+150°$ C is preferred. While the reaction does not necessarily require a solvent, the reaction may be carried out with increased facility if use is made, as a catalyst, of one of inorganic acids such as hydrochloric acid, hydrobromic acid, sulfuric acid, nitric acid, etc.; organic acids such as benzenesulfonic acid, toluenesulfonic acid, etc.; Lewis acids such as zinc chloride, aluminum chloride, boron trifluoride, etc.; and so forth.

By the foregoing procedure is produced a compound having general formula [IV]. The reaction mixture thus obtained may be directly subjected to the next reaction or, alternatively, may be isolated in a conventional manner before being used in the next reaction.

The reaction of compound [IV] with compound [V] is carried out in the presence of an appropriate solvent or in the absence of a solvent. Where a solvent is employed, it may be any of the solvents that will not interfere with the contemplated reaction, such as water, benzene, toluene, xylene, ligroin, dioxane, tetrahydrofuran, chloroform, methanol and ethanol and mixtures of two or more of such solvents. The proportion of amine [V] to be reacted with compound [IV] is not less than one molecular equivalent, and a large excess of said amine may be employed so as to let it act also as a solvent. An appropriate temperature may be selected from among the range of $-10°$ to $+250°$ C. While the reaction is normally conducted at atmospheric pressure, it may be carried out at elevated or reduced pressure. Particularly in the case that the amine [V] is low-boiling, the reaction in a sealed tubular reactor or in an autoclave may be more advantageous.

Compound [I] where $R^1$ and/or $R^2$ is hydroxyl can also be obtained per se known ether cleavage of the corresponding alkoxy compound [I], for example, by reacting the alkoxy compound [I] with hydrogen bromide, hydrogen iodide or a Lewis acid such as boron trichloride, boron trifluoride and aluminum chloride.

The compound [I] according to the present invention may be easily separated from the reaction mixture by conventional purification and separation procedures such as distillation, filtration, recrystallization, column chromatography and so forth. Because of the presence of at least one asymmetrical carbon atom within the molecule of compound [I], the compound exists as a mixture of two or more optical isomers. While this mixture as such may normally be employed as a drug or an intermediate therefor, it may be resolved and isolated as independent isomers by conventional resolution procedures for example by causing it to form a salt with an optically active acid.

The compound [I] according to the present invention may be made into the addition salt of a pharmacologically acceptable acid in a known manner, the salts of pharmacologically acceptable acid being exemplified by the salts of inorganic acids (e.g. hydrochloride, hydrobromide, sulfate, etc.), organic acids (e.g. maleate, fumarate, tartrate, methanesulfonate, etc.) and so forth.

The compounds of general formula [I] and their salts have antidepressant, analgesic, diuretic, anti-inflammatory, muscle relaxing, vasodilator, hypotensive and other pharmacologic activities for mammals including human beings and, as such, are of value as antidepressants, analgesics, diuretics, anti-inflammatory agents, muscle relaxant, hypotensives and cerebral circulation remedies for mammals.

When the contemplated compound of this invention is used as such a drug, it may be orally or parenterally administered, either as it is or after formulation into such dosage forms as powders, granules, tablets, capsules, injections, aerosol mists, etc. by admixture with suitable pharmaceutically acceptable carriers, excipients or/and diluents. While the optimum dosage varies with kinds of mammals, the disease to be treated, symptoms, particular species of compound [I] and route of administration, it may be somewhere between about 10 mg. and 1000 mg. daily by the oral route or about 1 to 50 mg. daily by the intravenous route per adult human when the compound is used as a hypotensive.

The compounds [I] according to the present invention are also of use as intermediates for the synthesis of various medicines and drugs.

EXAMPLE 1

To a mixture of 10 g. of 3,4-dimethoxyphenethylalcohol and 10 g. of chloroacetaldehyde diethyl acetal was added 14 ml of 10% hydrochloric acid. The mixture was stirred at 90° C for 10 minutes. After cooling, 100 ml of water was added to the reaction mixture, followed by extraction with benzene. The extract was rinsed with water, dried and concentrated under reduced pressure. By the above procedure was obtained 12 g of 1-chloromethyl-6,7-dimethoxyisochroman as an oil colored light-tan.

NMR spectrum (CDCl$_3$) δ: 3.13(2H,t,J=5Hz,—CH$_2$—Cl); 4.15(3H,s,CH$_3$); 4.19(3H,s,CH$_3$); 4.33–4.25(4H,m,CH$_2$); 5.28(1H,d,J=5Hz); 7.12(2H,s, phenyl protons).

A mixture of 5 g. of 1-chloromethyl-6,7-dimethoxyisochroman and 10 g of morpholine was heated at 150° C for 6 hours and, after cooling, the reaction mixture was concentrated under reduced pressure. The residue was diluted with 50 ml of water and extracted with chloroform. The extract was rinsed with water, dried and concentrated under reduced pressure. To the residue was added alcoholic hydrochloric acid and the resultant hydrochloride was crystallized by the addition of ethyl ether. The above procedure provided 5.1 g of 6,7-dimethoxy-1-morpholinoisochroman hydrochloride as colorless needles melting at 237°–239° C.

Elemental analysis for C$_{16}$H$_{23}$O$_4$N.HCl.H$_2$O. Calcd: C, 55.24; H, 7.53; N, 4.03. Found: C, 55.50; H, 7.30; N, 4.06.

EXAMPLE 2

To a mixture of 10 g of 2,5-dimethoxyphenethyl alcohol and 10 g of chloroacetaldehyde diethyl acetal was added 14 ml of 10% hydrochloric acid and, after stirring at 80°–90° C for 1 hour, the reaction mixture was diluted with 100 ml of water and extracted with benzene. The extract was rinsed with water, dried and concentrated under reduced pressure. The residue was recrystallized from a solvent mixture of ether and petroleum ether. By the above procedure was obtained 14 g of 1-chloromethyl-5,8-dimethoxyisochroman as colorless needles, melting point: 101°–102° C.

Elemental analysis for C$_{12}$H$_{15}$O$_3$Cl. Calcd: C, 59.38; H, 6.19. Found: C, 59.47; H, 6.27.

In a sealed tube, 3.0 g of 1-chloromethyl-5,8-dimethoxyisochroman and 6.0 g of N-methylpiperazine were heated at 150°–160° C for 16 hours. After cooling, the reaction mixture was diluted with 200 ml of water and the oily precipitate was extracted with chloroform. The extract was rinsed with water, dried and concentrated under reduced pressure. The residue was chromatographed on a column of silica gel, elution being carried out with a solvent mixture of acetone, benzene and methanol (2:2:1). The oil thus obtained was converted to the fumarate and recrystallized from a solvent mixture of methanol and ether. By this procedure was obtained 1.3 g of 5,8-dimethoxy-1-(4-methylpiperazinyl)-methylisochroman fumarate as pale-yellow needles, melting point: 188°–191° C.

Elemental analysis for $C_{17}H_{26}O_3N_2 \cdot C_4H_4O_4$. Calcd: C, 59.70; H, 7.16; N, 6.63. Found: C, 59.58; H, 7.00; N, 6.33.

EXAMPLE 3

A mixture of 30 g of 3-methoxyphenethyl alcohol, 30 g of chloroacetaldehyde diethyl acetal and 50 ml of concentrated hydrochloric acid was heated at 60°–80° C for 30 minutes, and, after cooling, water was added to the reaction mixture. The resultant oil was extracted into ethyl acetate, rinsed with water and dried. By this procedure was obtained 4.0 g of 1-chloromethyl-6-methoxyisochroman as an oil.

NMR spectrum (CDCl₃) δ: 2.80(2H,t,J=5Hz,—CH₂—Cl), 3.75 (3H,s,CH₃), 5.00(1H,d,J=5Hz), 6.60–6.80(2H,m,phenyl protons), 7.10(1H,d,J=8Hz, phenyl protons).

A mixture of 5.0 g of 1-chloromethyl-6-methoxyisochroman and 30 ml of diethylamine was heated in a sealed tube at 150°–160° C for 21 hours and, after cooling, the reaction mixture was concentrated under reduced pressure. The residue was diluted with 100 ml of water and extracted with chloroform. The extract was rinsed with water, dried and concentrated under reduced pressure. The residue was chromatographed on a column of silica gel, and elution was carried out with a 1:2 mixture of benzene and methanol. The oily product thus obtained was converted to the fumarate and recrystallized from a mixture of methanol and ether. By the above procedure was obtained 1.9 g of 1-diethylaminomethyl-6-methoxyisochroman fumarate as colorless prisms.

Elemental analysis for $C_{15}H_{23}O_2N \cdot C_4H_4O_4 \cdot H_2O$. Calcd: C, 59.51; H, 7.62; N, 3.65. Found: C, 59.49; H, 7.92; N, 3.21.

EXAMPLE 4

A mixture of 30 g of 2,3-dimethoxyphenethyl alcohol, 30 g of chloroacetaldehyde diethyl acetal and 50 ml of concentrated hydrochloric acid was heated at 60°–80° C for 1 hour and, after cooling, the reaction mixture was diluted with water. The resultant oily precipitate was extracted into ethyl acetate, rinsed with water, dehydrated and concentrated under reduced pressure. The residue was then recrystallized from petroleum ether. By the above procedure was obtained 33 g of 1-chloromethyl-5,6-dimethoxyisochroman as colorless needles, melting point: 63°–65° C.

Elemental analysis for $C_{12}H_{15}O_3Cl$. Calcd: C, 59.38; H, 6.23. Found: C, 59.34; H, 6.38.

A solution of 5.0 g of 1-chloromethyl-5,6-dimethoxyisochroman and 6.7 g of N-(2-pyridyl)piperazine in 50 ml of ethanol was refluxed for 11 hours, after which time the ethanol was distilled off under reduced pressure. The residue was diluted with 100 ml of water and extracted with chloroform. The extract was rinsed with water, dried and concentrated under reduced pressure. The residue was chromatographed on a column of silica gel, elution being carried out with acetone-benzene (4:1). The resultant oil was converted to the fumarate and recrystallized from a solvent mixture of ethanol and ether. By this procedure was obtained 3.6 g of 5,6-dimethoxy-1-[4-(2-pyridyl)-piperazinylmethyl]isochroman fumarate as colorless needles, melting point: 207°–209° C.

Elemental analysis for $C_{21}H_{27}O_3N_3 \cdot C_4H_4O_4$. Calcd: C, 61.84; H, 6.44; N, 8.66. Found: C, 61.60; H, 6.20; N, 8.67.

EXAMPLE 5

In a sealed tube at 150°–160° C, 5 g of the 1-chloromethyl-6,7-dimethoxyisochroman obtained in Example 1 and 10 ml of isopropylamine were heated for 15 hours. After cooling, the reaction mixture was concentrated under reduced pressure and an ethereal solution of fumaric acid was added to the residue. The resultant fumarate was recrystallized from a solvent mixture of ethanol and ether. By the above procedure was obtained 4.6 g of 1-isopropylaminomethyl-6,7-dimethoxyisochroman fumarate as colorless needles, melting point: 201°–202° C.

Elemental analysis for $C_{15}H_{23}O_3N \cdot C_4H_4O_4$. Calcd: C, 59.83; H, 7.14; N, 3,67. Found: C, 59.88; H, 7.05; N, 4.06.

EXAMPLE 6

To a mixture of 20 g of 3,4-dimethoxyphenethyl alcohol and 22 g of β-chloropropionaldehyde diethyl acetal was added 30 ml of concentrated hydrochloric acid, followed by heating at 60°–80° C with stirring for 25 minutes. After cooling, the reaction mixture was diluted with 100 ml of water and extracted with ethyl acetate. The extract was rinsed with water, dried and concentrated under reduced pressure.

The resultant oil was chromatographed on a column of silica gel, followed by elution with a 1:9 mixture of acetone and benzene. By this procedure was obtained 6.9 g of 1-(2-chloroethyl)-6,7-dimethoxyisochroman as a colorless oil. Together with 10 ml of morpholine, 0.9 g of this oil was heated under reflux for 3.5 hours. The reaction mixture was concentrated under reduced pressure and the concentrate was diluted with 100 ml of water and extracted with ethyl acetate. The organic layer was rinsed with water, dried and concentrated under reduced pressure. The residue was dissolved in 10 ml of ethanol, followed by the addition of an ethereal solution of fumaric acid. The mixture was allowed to stand in the cold, whereupon 0.5 g of 6,7-dimethoxy-1-(2-morpholinoethyl)-isochroman fumarate was obtained as colorless needles, melting point: 161°–163° C.

Elemental analysis for $C_{15}H_{25}O_4N \cdot C_4H_4O_4$. Calcd: C, 57.13; H, 7.32; N, 3.51. Found: C, 57.55; H, 7.02; N, 3.44.

EXAMPLE 7

To a mixture of 20 g of 2,3-dimethoxyphenethyl alcohol and 22 g of β-chloropropionaldehyde diethyl acetal was added 30 ml of concentrated hydrochloric acid, followed by heating at 60°–85° C with stirring for 25 minutes. After cooling, the reaction mixture was diluted with 100 ml of water and extracted with ethyl acetate. The extract was rinsed with water, dehydrated, treated with activated carbon and concentrated under reduced pressure. By the above procedure was obtained 24 g of 1-(2-chloroethyl)-5,6-dimethoxyisochroman as a colorless oil. Together with 15 ml of piperidine, 3 of this oil was heated under reflux for 2 hours, with constant stirring. After cooling, the reaction mixture was concentrated and the residue was diluted with 100 ml of water and extracted with ethyl acetate. The extract was rinsed with water, dried and concentrated under reduced pressure. The oily residue was chromatographed on a column of silica gel, elution being carried out with a 9:1 mixture of chloroform and methanol. By this procedure was obtained 2.7 g of 5,6-dimethoxy-1-(2-piperidinoethyl)isochroman as an oil. This oil was dissolved in 10 ml of alcoholic hydrochloric acid, followed by addition of ethyl ether. The mixture was left standing, whereby 1.5 g of 5,6-dimethoxy-1-(2-piperidinoethyl)-isochroman hydrochloride was obtained as colorless crystals, melting point: 178°–180° C.

Elemental analysis, for $C_{18}H_{27}O_3N \cdot HCl$. Calcd: C, 63.23; H, 8.26; N, 4.10. Found: C, 63.07; H, 8.23; N, 4.27.

EXAMPLES 8–71

In a similar manner to one of Examples 1 to 7, the compounds given in Table 1 were obtained.

Table 1

| Example No. | $X^1$ | $X^2$ | $X^3$ | $X^4$ | n | Z | A (Salt) | m.p. (° C) |
|---|---|---|---|---|---|---|---|---|
| 8 | H | OCH₃ | OCH₃ | H | 1 | piperidino | Fumarate | 155–157 |
| 9 | H | OCH₃ | OCH₃ | H | 1 | —NHCH₂CH₂-phenyl | Fumarate | 190–192 |
| 10 | H | OCH₃ | OCH₃ | H | 1 | —N(piperazinyl)-2-pyridyl | Fumarate | 201–203 |
| 11 | H | OCH₃ | OCH₃ | H | 1 | —NHC(CH₃)₃ | ½ Fumarate | 220–221 |
| 12 | H | OCH₃ | OCH₃ | H | 1 | —N(C₂H₅)₂ | Fumarate | 135–138 |
| 13 | H | OH | OH | H | 1 | morpholino | HBr | 248–251 |
| 14 | H | OH | OH | H | 1 | —NHC(CH₃)₃ | HBr | 200–202 |
| 15 | H | OH | OH | H | 1 | —NHCH(CH₃)₂ | HBr | 169–171 |
| 16 | H | OH | OH | H | 1 | piperidino | HBr | 235–237 |
| 17 | OCH₃ | OCH₃ | H | H | 1 | —N(C₂H₅)₂ | Fumarate | 151.5–153.5 |
| 18 | OCH₃ | OCH₃ | H | H | 1 | —N(4-methylpiperazinyl) | 2HCl | 230 |
| 19 | OCH₃ | OCH₃ | H | H | 1 | —N(4-phenylpiperazinyl) | — | 114–115 |
| 20 | OCH₃ | OCH₃ | H | H | 1 | —NHCH(CH₃)₂ | Fumarate | 164–168 |
| 21 | OCH₃ | OCH₃ | H | H | 1 | morpholino | Fumarate | 171–178 |
| 22 | OCH₃ | OCH₃ | H | H | 1 | piperidino | HCl | 205–209 |
| 23 | OCH₃ | OCH₃ | H | H | 1 | —NHC(CH₃)₃ | Fumarate | 188–192 |
| 24 | OH | OH | H | H | 1 | morpholino | HBr | 234–235 |
| 25 | OH | OH | H | H | 1 | piperidino | HBr | 237–238 |
| 26 | OH | OH | H | H | 1 | —NHC(CH₃)₃ | HBr | 228–230 |
| 27 | OH | OH | H | H | 1 | —NHCH(CH₃)₂ | HBr | 209–210 |
| 28 | H | OCH₃ | H | H | 1 | —NHC(CH₃)₃ | Fumarate | 186–190 |
| 29 | H | OCH₃ | H | H | 1 | —N(piperazinyl)-2-pyridyl | Fumarate | 196–198 |

Table 1-continued

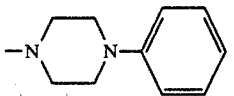

| Example No. | X¹ | X² | X³ | X⁴ | n | Z | A (Salt) | m.p. (° C) |
|---|---|---|---|---|---|---|---|---|
| 30 | H | OCH₃ | H | H | 1 | 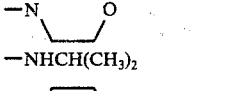 | — | 143–144 |
| 31 | H | OCH₃ | H | H | 1 | 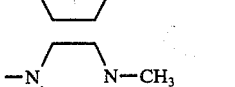 | Fumarate | 146–148 |
| 32 | H | OCH₃ | H | H | 1 | —NHCH(CH₃)₂ | Fumarate | 184–189 |
| 33 | H | OCH₃ | H | H | 1 | 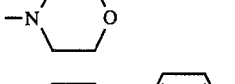 | HCl | 216–226 |
| 34 | H | OCH₃ | H | H | 1 | 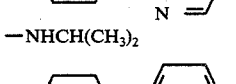 | 2HCl | 205 |
| 35 | OCH₃ | H | H | OCH₃ | 1 | 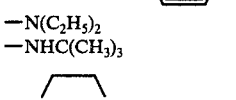 | Fumarate | 144–145 |
| 36 | OCH₃ | H | H | OCH₃ | 1 | 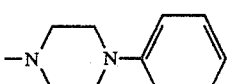 | 2HCl | 230–232 |
| 37 | H | OH | H | H | 1 | —NHCH(CH₃)₂ | HBr | 245–246 |
| 38 | H | OCH₃ | OCH₃ | H | 2 | 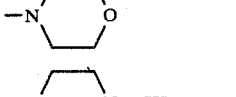 | 2HCl | 150–154 |
| 39 | OCH₃ | OCH₃ | H | H | 2 | —N(C₂H₅)₂ | HCl | 181–183 |
| 40 | OCH₃ | OCH₃ | H | H | 2 | —NHC(CH₃)₃ | ½ Fumarate | 234–237 |
| 41 | OCH₃ | OCH₃ | H | H | 2 | 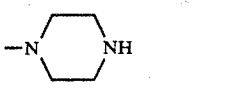 | 2HCl | 257–267 |
| 42 | OCH₃ | OCH₃ | H | H | 2 | 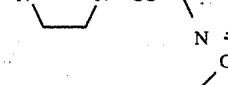 | 2HCl | 197–202 |
| 43 | OCH₃ | OCH₃ | H | H | 1 | 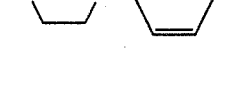 | Fumarate | 175–177 |
| 44 | OH | OH | H | H | 1 |  | 2HBr | 256–259 |
| 45 | OCH₃ | OCH₃ | H | H | 1 |  | HCl | 240 |
| 46 | OCH₃ | OCH₃ | H | H | 1 |  | 2HCl | 245–249 |
| 47 | OCH₃ | OCH₃ | H | H | 2 |  | 2HCl | 200–205 |

Table 1-continued

| Example No. | $X^1$ | $X^2$ | $X^3$ | $X^4$ | n | Z | A (Salt) | m.p. (° C) |
|---|---|---|---|---|---|---|---|---|
| 48 | OCH₃ | OCH₃ | H | H | 2 | piperazinyl-C₆H₄-4-OCH₃ | 2HCl | 193–195 |
| 49 | H | OCH₃ | OCH₃ | H | 2 | piperazinyl-C₆H₃-3,4-(OCH₃)₂ | 2HCl | 185–187 |
| 50 | H | OCH₃ | OCH₃ | H | 2 | piperazinyl-C₆H₄-4-OCH₃ | 2HCl | 143–148 |
| 51 | H | OCH₃ | H | H | 2 | piperazinyl-C₆H₃-3,4-(OCH₃)₂ | 2HCl | 183–185 |
| 52 | OCH₃ | OCH₃ | H | H | 2 | piperazinyl-NH | 2HCl | 257–260 |
| 53 | OCH₃ | OCH₃ | H | H | 2 | piperazinyl-CO-(2-pyridyl) | 2HCl | 190–192 |
| 54 | H | OCH₃ | OCH₃ | H | 2 | piperazinyl-NH | 2HCl | 255–257 |
| 55 | H | OCH₃ | OCH₃ | H | 2 | piperazinyl-(2-pyridyl) | 2HCl | 201–204 |
| 56 | H | OCH₃ | OCH₃ | H | 2 | piperazinyl-C₆H₄-3-Cl | 2HCl | 117–118 |
| 57 | H | OCH₃ | OCH₃ | H | 2 | piperazinyl-C₆H₄-4-Cl | 2HCl | 180–182 |
| 58 | H | OCH₃ | OCH₃ | H | 2 | piperazinyl-CO-(2-furyl) | HCl | 222–224 |
| 59 | H | OCH₃ | OCH₃ | H | 2 | piperazinyl-CO-C₆H₂-3,4,5-(OCH₃)₃ | HCl | 215–217 |
| 60 | OCH₃ | OCH₃ | H | H | 2 | piperazinyl-(2-pyridyl) | 2HCl | 221–223 |

Table 1-continued

Structure:

$$X^1, X^2, X^3, X^4 \text{ substituted benzene fused to ring with } -O-CH(CH_2)_n-Z \cdot A$$

| Example No. | $X^1$ | $X^2$ | $X^3$ | $X^4$ | n | Z | A (Salt) | m.p. (° C) |
|---|---|---|---|---|---|---|---|---|
| 61 | OCH₃ | OCH₃ | H | H | 2 | −N(piperazinyl)N−(3-chlorophenyl) | 2HCl | 159–160 |
| 62 | OCH₃ | OCH₃ | H | H | 1 | −N(piperazinyl)N−(4-methoxyphenyl) | Fumarate | 214–216 |
| 63 | OCH₃ | OCH₃ | H | H | 2 | −N(piperazinyl)N−(4-chlorophenyl) | 2HCl | 179–181 |
| 64 | H | OCH₃ | H | H | 1 | −NHCH(CH₃)CH₂CH₂−phenyl | HCl | 148–151 |
| 65 | H | OCH₃ | OCH₃ | H | 1 | −NHCH(CH₃)CH₂CH₂−phenyl | HCl | 207–209 |
| 66 | H | −O−CH₂−O− | | H | 2 | −N(piperazinyl)N−(2-pyridyl) | 2HCl | 221 |
| 67 | H | −O−CH₂−O− | | H | 1 | −N(piperazinyl)N−(2-pyridyl) | 2HCl | 223 |
| 68 | H | −O−CH₂−O− | | H | 2 | −N(piperazinyl)N−phenyl | 2HCl | 207–209 |
| 69 | OCH₃ | OCH₃ | H | H | 1 | −N(piperazinyl)N−(4-chlorophenyl) | 2HCl | 211–213 |
| 70 | OCH₃ | OCH₃ | H | H | 1 | −N(piperazinyl)N−(3-chlorophenyl) | 2HCl | 244–245 |
| 71 | OCH₃ | OCH₃ | H | H | 2 | −N(piperazinyl)N−CH(phenyl)₂ | 2HCl | 225 |

What is claimed is:
1. A compound of the formula

[Structural formula: isochroman with R¹, R² substituents on aromatic ring, and (CH₂)ₙ–N(piperazine)N–R³ chain at position 1]

wherein R¹ ia hydrogen, lower alkoxy or hydroxyl and R² is lower alkoxy or hydroxyl of R¹ and R² when taken together form alkylenedioxy; R³ is pyridyl, 3 or 4-chlorophenyl, 4-methoxyphenyl, 3,4-dimethoxyphenyl, 3,4,5-trimethoxyphenyl or phenyl and $n$ is 1 or 2 or pharmaceutically acceptable salts thereof.

2. A compound claimed in claim 1, which is 5,6-dimethoxy-1-[4-(2-pyridyl)piperazinylmethyl]-isochroman.

3. A compound claimed in claim 1, which is 6,7-dimethoxy-1-[4-(2-pyridyl)piperazinylmethyl]-isochroman.

4. A compound claimed in claim 1, which is 6-methoxy-1-[4-(2-pyridyl)piperazinylmethyl]-isochroman.

5. A compound claimed in claim 1, which is 5,8-dimethoxy-1-[4-(2-pyridyl)piperazinylmethyl]-isochroman.

6. A compound claimed in claim 1, which is 6,7-dimethoxy-1-{2-[4-(2-pyridyl)piperazinyl]-ethyl}-isochroman.

7. A compound claimed in claim 1, which is 5,6-dimethoxy-1-{2-[4-(2-pyridyl)piperazinyl]ethyl}-isochroman.

8. A compound claimed in claim 1, which is 6,7-methylenedioxy-1-{2-[4-(2-pyridyl)piperazinyl]-ethyl}-isochroman.

9. A compound claimed in claim 1, which is 6,7-methylenedioxy-1-[4-(2-pyridyl)-piperazinyl]-methylisochroman.

10. A compound claimed in claim 1, wherein R₃ represents phenyl.

11. A compound claimed in claim 1, which is 5,6-dimethoxy-1-(4-phenylpiperazinyl)methylisochroman.

12. A compound claimed in claim 1, which is 6-methoxy-1-(4-phenylpiperazinyl)methylisochroman.

13. A compound claimed in claim 1, which is 6,7-dimethoxy-1-[2-(4-phenylpiperazinyl)ethyl]-isochroman.

14. A compound claimed in claim 1, which is 5,6-dimethoxy-1-[2-(4-phenylpiperazinyl)ethyl]-isochroman.

15. A compound claimed in claim 1, which is 6,7-methylenedioxy-1-[2-(4-phenylpiperazinyl)-ethyl]-isochroman.

16. A compound claimed in claim 1, wherein R³ represents 3-chlorophenyl.

17. A compound claimed in claim 1, which is 6,7-dimethoxy-1-{2-[4-(3-chlorophenyl)piperazinyl]ethyl}•isochroman.

18. A compound claimed in claim 1, which is 5,6-dimethoxy-1-{2-[4-(3-chlorophenyl)piperazinyl]ethyl}•isochroman.

19. A compound claimed in claim 1, which is 5,6-dimethoxy 1-[4-(3-chlorophenyl)piperazinylmethyl]isochroman.

20. A compound claimed in claim 1, wherein R³ represents 4-chlorophenyl.

21. A compound claimed in claim 1, which is 6,7-dimethoxy-1-{2-[4-(4-chlorophenyl)piperazinyl]ethyl}•isochroman.

22. A compound claimed in claim 1, which is 5,6-dimethoxy-1-{2-[4-(4-chlorophenyl)piperazinyl]ethyl}•isochroman.

23. A compound claimed in claim 1, which is 5,6-dimethoxy 1-[4-(4-chlorophenyl)piperazinylmethyl]isochroman.

24. A compound of the formula:

[Structural formula: 5,6-dimethoxyisochroman bearing at position 1 a –CH₂CH₂–N(piperazine)N–CH(phenyl)₂ substituent, with OCH₃ and CH₃O– groups on the aromatic ring]

and pharmaceutically acceptable salts thereof.

* * * * *